(12) United States Patent
Darouiche et al.

(10) Patent No.: US 7,452,345 B2
(45) Date of Patent: Nov. 18, 2008

(54) ANTI-INFECTIVE ENDOTRACHEAL TUBE

(75) Inventors: Rabih O. Darouiche, Houston, TX (US); Randall A. Prince, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 723 days.

(21) Appl. No.: 10/664,519

(22) Filed: Sep. 17, 2003

(65) Prior Publication Data

US 2004/0116845 A1 Jun. 17, 2004

Related U.S. Application Data

(60) Provisional application No. 60/411,177, filed on Sep. 17, 2002.

(51) Int. Cl.
*A61B 17/20* (2006.01)
(52) U.S. Cl. ............... 604/22; 600/439; 600/466; 604/264; 604/265; 128/207.14
(58) Field of Classification Search ............... 600/437, 600/439, 462; 128/207.14, 207.15; 604/22, 604/264, 265
See application file for complete search history.

(56) References Cited

U.S. PATENT DOCUMENTS

| 3,087,493 A | 4/1963 | Schossow | 128/351 |
|---|---|---|---|
| 3,981,299 A | 9/1976 | Murray | 128/349 B |
| 4,446,864 A | 5/1984 | Watson et al. | 128/207.14 |
| 4,717,379 A | 1/1988 | Ekholmer | 604/43 |
| 4,886,059 A * | 12/1989 | Weber | 128/207.15 |
| 4,967,759 A * | 11/1990 | Teves | 600/528 |
| 5,143,062 A | 9/1992 | Peckham | 128/207.14 |
| 5,313,939 A | 5/1994 | Gonzalez | 128/207.14 |
| 5,389,074 A | 2/1995 | Parker et al. | 604/96 |
| 5,499,625 A | 3/1996 | Frass et al. | 128/207.15 |
| 5,544,648 A | 8/1996 | Fischer, Jr. | 128/207.14 |
| 5,582,167 A | 12/1996 | Joseph | 128/207.15 |
| 5,638,812 A | 6/1997 | Turner | 128/207.14 |
| 5,803,078 A | 9/1998 | Brauner | 124/207.14 |
| 5,819,723 A | 10/1998 | Joseph | 128/207.14 |
| 6,235,024 B1 | 5/2001 | Tu | 606/41 |
| 6,428,491 B1 * | 8/2002 | Weiss | 601/2 |
| 6,878,287 B1 * | 4/2005 | Marais | 210/748 |
| 6,887,727 B2 * | 5/2005 | Takeuchi et al. | 438/22 |

* cited by examiner

*Primary Examiner*—Brian L. Casler
*Assistant Examiner*—John F Ramirez
(74) *Attorney, Agent, or Firm*—Tim Headley

(57) ABSTRACT

A multi-lumen endotracheal tube has means for coating an inside and an outside surface of the endotracheal tube with antimicrobial and antibiofilm agents; means for releasing antimicrobial and antibiofilm agents from the endotracheal tube; means for using electrical current to enhance the efficacy of the antimicrobial and antibiofilm agents; and means for using ultrasound energy to enhance the efficacy of the antimicrobial and antibiofilm agents. In another feature of the present invention, the multi-lumen tube further has an outer lumen, and a concentric inner lumen, and the outer lumen contains the means for coating, the means for releasing, the means for using electrical current, and the means for using ultrasound energy. In another feature of the present invention, the inside and outside surfaces have a surface coating to reduce the buildup of bacteria and biofilm on the surface.

9 Claims, 3 Drawing Sheets

ANTI-INFECTIVE ENDOTRACHEAL TUBE

CROSS-REFERENCE TO RELATED APPLICATIONS

This application claims the benefit of the following U.S. Provisional Application: No. 60/411,177, filed Sep. 17, 2002.

STATEMENT REGARDING FEDERALLY SPONSORED RESEARCH OR DEVELOPMENT

Not Applicable.

REFERENCE TO A "SEQUENTIAL LISTING," A TABLE, OR A COMPUTER PROGRAM LISTING APPENDIX SUBMITTED ON A COMPACT DISC

Not Applicable.

BACKGROUND OF THE INVENTION

1. Field of the Invention

The invention involves catheters usable in medical treatments of a condition of a living body, and more particularly, catheters that can release antimicrobial agents, antibiofilm agents, electric radiation, or ultrasound radiation.

2. Description of Related Art

The related art can be reviewed via the following issued patents, the full disclosures of which are all incorporated herein by this reference:

U.S. Pat. No. 6,235,024 Catheters System Having Dual Ablation Capability

U.S. Pat. No. 5,819,723 Methods And Apparatus For Reducing Tracheal Infection

U.S. Pat. No. 5,638,812 Coated Medico-Surgical Devices

U.S. Pat. No. 5,582,167 Methods And Apparatus For Reducing Tracheal Infection Using Subglottic Irrigation, Drainage And Servoregulation Of Endotracheal Tube Cuff Pressure U.S. Pat. No. 5,544,648 Device For Intratracheal Ventilation And Intratracheal Pulmonary Ventilation Including Reverse Venturi U.S. Pat. No. 5,499,625 Esophageal-Tracheal Double Lumen Airway U.S. Pat. No. 5,389,074 Body Insertion Tube With Anesthetic Jacket U.S. Pat. No. 5,313,939 Endotracheal Tube For Topical Substance Delivery And Associated Method Of Use U.S. Pat. No. 5,143,062 Endotracheal Tube Having Irrigation Means U.S. Pat. No. 4,446,864 Emergency Ventilation Tube U.S. Pat. No. 3,087,493 Endotracheal Tube Although some prior endotracheal tubes have means for releasing into a body various medications, including steroids, antibiotics, irrigants, lubricants, antimicrobial agents, and antibiofilm agents, those same endotracheal tubes do not also have means for releasing into a body electrical energy, or means for releasing ultrasound energy, for therapeutic purposes. What is needed is an endotracheal tube that has means for releasing both medications and energy, for both treatment and prevention of physical problems.

BRIEF SUMMARY OF THE INVENTION

A multi-lumen endotracheal tube comprises means for coating an inside and an outside surface of the endotracheal tube with antimicrobial and antibiofilm agents; means for releasing antimicrobial and antibiofilm agents from the endotracheal tube; means for using electrical current to enhance the efficacy of the antimicrobial and antibiofilm agents; and means for using ultrasound energy to enhance the efficacy of the antimicrobial and antibiofilm agents. In another feature of the present invention, the multi-lumen tube further comprises an outer lumen, and a concentric inner lumen, and the outer lumen contains the means for coating, the means for releasing, the means for using electrical current, and the means for using ultrasound energy. In another feature of the present invention, the inside and outside surfaces have a surface coating to reduce the buildup of bacteria on the surface.

DETAILED DESCRIPTION OF THE INVENTION

Figure 1:
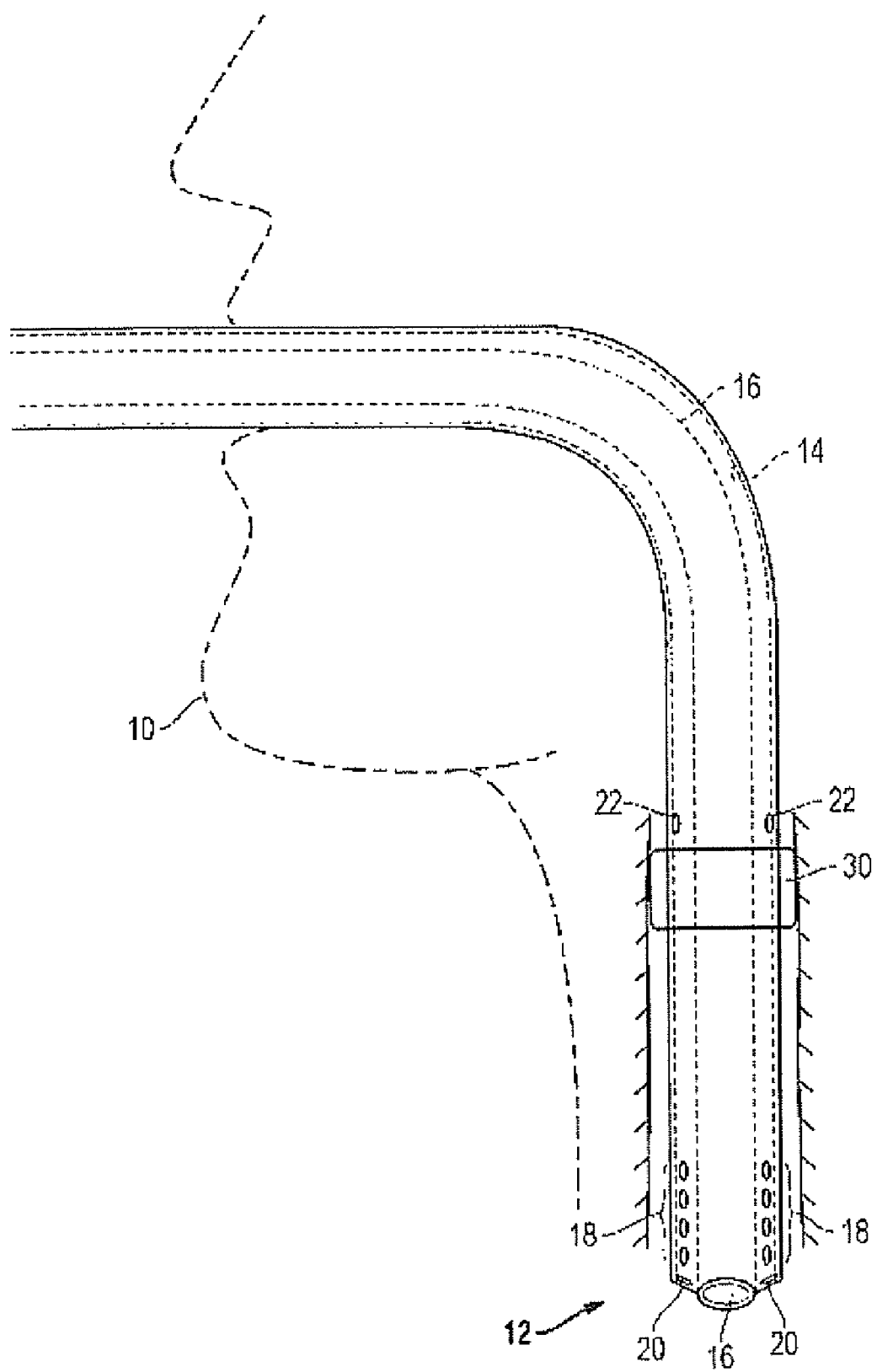
FIG. 1 is a schematic side view of the tube of the present invention, illustrated in use with a patient.

Referring to FIG. 1, a patient 10 has a tube 12 according to the present invention inserted in him. The tube 12 includes an outer lumen 14 and an inner lumen 16. The inner lumen 16 is a tube that is concentric with the lumen 14, provides structural support, and serves as an airway for the patient to breathe. Both an outside surface of the outer lumen 14, and an inside surface of the inner lumen 16 have both antibiofilm and antimicrobial surface coatings to reduce the buildup of bacteria and biofilm on the surfaces.

Tubes with inner and outer concentric lumens are known in the art, such as the tubes disclosed in the following patents, the full disclosures of which are all incorporated herein by this reference:

tube in U.S. Pat. No. 5,819,723 tube in U.S. Pat. No. 5,582,167 multiple lumen tracheal or endotracheal tube in U.S. Pat. No. 5,544,648 tube and chamber in U.S. Pat. No. 5,389,074 tube member, lumen, and conduit members in U.S. Pat. No. 5,313,939 lumens and in U.S. Pat. No. 5,143,062

"first, inner tube and a larger diameter, outer tube" in U.S. Pat. No. 4,446,864 outer and inner walls and in U.S. Pat. No. 3,087,493

Figure 2:
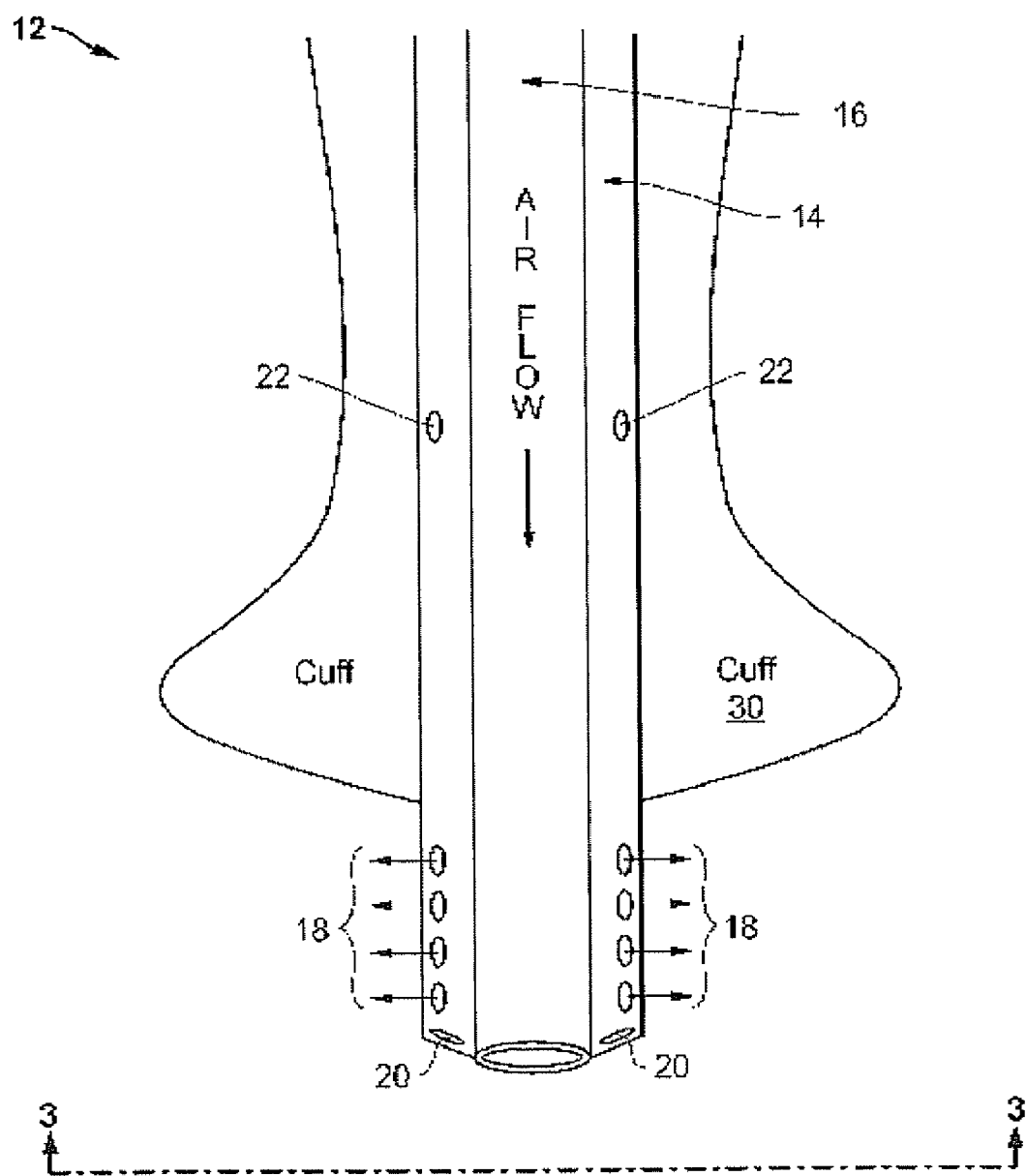
FIG. 2 is a side view of the tube of the present invention.

Referring to FIG. 2, the outer lumen 14 includes a series of ports 18 for dispensing both antimicrobial and antibiofilm agents. Ports in endotracheal tubes are known in the art, such as the ports disclosed in the following patents, the full disclosures of which are all incorporated herein by this reference:

outlets (for infusing drugs and monitoring pressure) in U.S. Pat. No. 5,544,648 perforations (for delivering anesthetics) in U.S. Pat. No. 5,389,074 openings (for delivering various medications, including steroids, antibiotics, irrigants, and lubricants) in U.S. Pat. No. 5,313,939 suction eye in U.S. Pat. No. 5,143,062

"Tube is provided with a plurality of radially extending openings which permit the passage of gas into and out of the interior of portion" in U.S. Pat. No. 4,446,864 ports (for introducing beneficial fluids) in U.S. Pat. No. 3,087,493

U.S. Pat. No. 5,638,812 discloses a tracheal tube having a surface coating to reduce the buildup of bacteria on the tube. The disclosure of such tube with such coating is incorporated herein by this reference.

The outer lumen 14 also includes spots 20 for radiating ultrasound waves, and spots 22 for radiating electrical waves. The following disclosures of U.S. Pat. No. 6,235,024 are incorporated herein by this reference:

ablation element, which includes a wall, which comprises an ultrasound transducer RF ablation means "A high frequency current generator means is part of the ablation catheter system, wherein an electrical conducting means is coupled from the generator to the ablation element. The high frequency energy generator means may comprise a switch means for switching high frequency energy to radiofrequency spectrum, ultrasound frequency spectrum, or radiofrequency/ultrasound frequency overlapped spectrum. This switch means is an operator-initiated action to the appropriate ablation mode selected from the group consisting of radiofrequency ablation mode, ultrasound ablation mode, and simultaneous radiofrequency and ultrasound ablation mode. In each mode, the energy delivery may be continuous, pulsed, programmed, and the like."

The method of operating the ablation catheter, as described in the patent.

It is easily understood by those skilled in this technology that if treatment other than ablation is desired, the operator may simply use lower power settings of the current generator. Thus, the operator of the present invention may use the spots 20 and 22 to enhance the activity of the antimicrobial agents delivered through the ports 18, against the organisms embedded within the biofilm.

Figure 3:
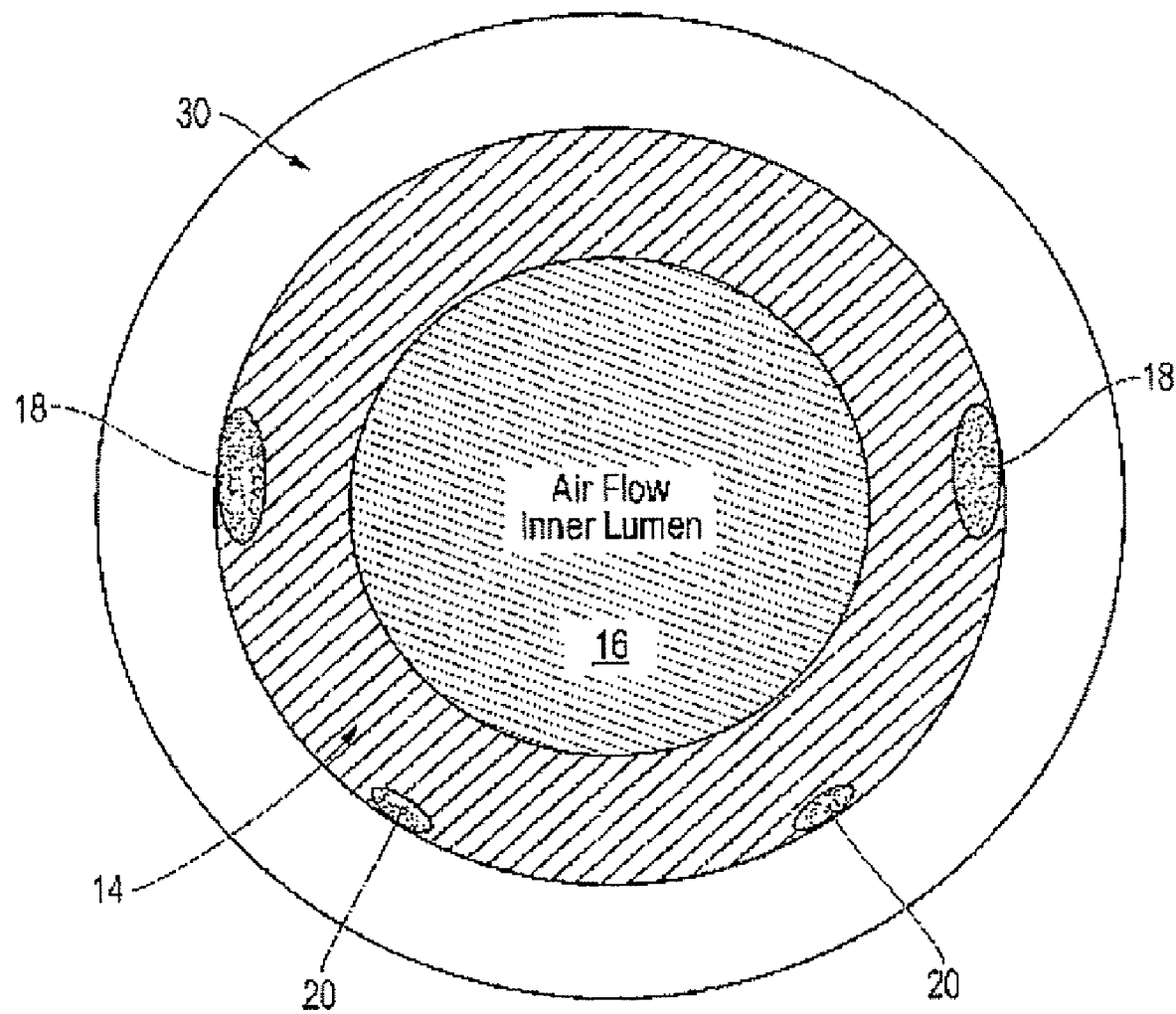
FIG. 3 is an end view of the tube of the present invention.

Referring to both FIG. 2 and FIG. 3, the tube 12 further includes a cuff 30. The cuff 30 is a standard cuff, known in the art, such as the cuffs disclosed in the following patents, the full disclosures of which are all incorporated herein by this reference:

cuff in U.S. Pat. No. 5,819,723
    cuff in U.S. Pat. No. 5,582,167
    cuffs in U.S. Pat. No. 5,499,625
    cuff in U.S. Pat. No. 5,389,074
    inflatable cuff in U.S. Pat. No. 5,143,062
    "occluding device" in U.S. Pat. No. 4,446,864

It should be understood that the invention is not intended to be limited to the specifics of the described preferred embodiments, but is defined by the accompanying claims. That is, although illustrative embodiments have been shown and described, a wide range of modification, changes, and substitution is contemplated in the foregoing disclosure. In some instances, some features of the disclosed embodiments may be employed without a corresponding use of the other features. Accordingly, it is appropriate that the appended claims be construed broadly and in a manner consistent with the scope of the invention.

What is claimed is:

1. A multi-lumen endotracheal tube comprising:
   a. means for coating an inside surface and an outside surface of the endotracheal tube with antimicrobial and antibiofilm agents;
   b. means for releasing antimicrobial and antibiofilm agents from the endotracheal tube;
   c. means for using electrical current to enhance the efficacy of the antimicrobial and antibiofilm agents; and
   d. means for using ultrasound energy to enhance the efficacy of the antimicrobial and antibiofllm agents.

2. The tube of claim 1, further comprising an outer lumen, and a concentric inner lumen.

3. The tube of claim 2, wherein the outer lumen contains the means for coating, the means for releasing, the means for using electrical current, and the means for using ultrasound energy.

4. The tube of claim 3, wherein the inside and outside surfaces have a surface coating to reduce the buildup of bacteria and biofllm.

5. A method of using a multi-lumen endotracheal tube in a human patient, comprising the steps of:
   a. coating inside and outside surfaces of the endotracheal tube with antimicrobial and antibiofilm agents;
   b. inserting the endotracheal tube in the patient;
   c. releasing antimicrobial and antibiofilm agents from the endotracheal tube;
   d. using electrical current to enhance the efficacy of the antimicrobial and antibiofilm agents; and
   e. using ultrasound energy to enhance the efficacy of the antimicrobial and antibiofilm agents.

6. The method of claim 5, wherein steps c-e are performed in any order.

7. The method of claim 6, wherein the tube comprises an outer lumen, and a concentric inner lumen.

8. The method of claim 7, wherein the outer lumen contains means for coating, means for releasing, means for using electrical current, and means for using ultrasound energy.

9. The method of claim 8, wherein the concentric inner lumen serves as an airway for the patient to breathe.

* * * * *